United States Patent
Sinha

(10) Patent No.: US 8,166,801 B2
(45) Date of Patent: May 1, 2012

(54) NON-INVASIVE FLUID DENSITY AND VISCOSITY MEASUREMENT

(75) Inventor: Dipen N. Sinha, Los Alamos, NM (US)

(73) Assignee: Los Alamos National Security, LLC, Los Alamos, NM (US)

(*) Notice: Subject to any disclaimer, the term of this patent is extended or adjusted under 35 U.S.C. 154(b) by 93 days.

(21) Appl. No.: 11/865,042

(22) Filed: Sep. 30, 2007

(65) Prior Publication Data

US 2009/0084178 A1    Apr. 2, 2009

(51) Int. Cl.
*G01N 9/00* (2006.01)
(52) U.S. Cl. ...................................... 73/32 A
(58) Field of Classification Search .......... 73/579, 73/861.355, 32 A
See application file for complete search history.

(56) References Cited

U.S. PATENT DOCUMENTS

| | | | |
|---|---|---|---|
| 5,741,980 A | 4/1998 | Hill et al. | 73/861.04 |
| 5,767,407 A * | 6/1998 | Sinha | 73/579 |
| 5,837,885 A | 11/1998 | Goodbread et al. | 73/32 A |
| 5,886,262 A * | 3/1999 | Sinha | 73/579 |
| 6,053,041 A | 4/2000 | Sinha | 73/290 V |
| 6,644,119 B1 * | 11/2003 | Sinha | 73/579 |
| 6,688,176 B2 * | 2/2004 | Storm et al. | 73/579 |
| 7,121,152 B2 | 10/2006 | Winston et al. | 73/861.42 |
| 2006/0010963 A1 * | 1/2006 | Bach et al. | 73/54.01 |
| 2009/0078050 A1 * | 3/2009 | Sinha | 73/632 |

* cited by examiner

*Primary Examiner* — Hezron E Williams
*Assistant Examiner* — Tamiko Bellamy
(74) *Attorney, Agent, or Firm* — Samuel M. Freund; Cochran Freund & Young Law Fir; Meredith H. Schoenfeld

(57) ABSTRACT

The noninvasively measurement of the density and viscosity of static or flowing fluids in a section of pipe such that the pipe performs as the sensing apparatus, is described. Measurement of a suitable structural vibration resonance frequency of the pipe and the width of this resonance permits the density and viscosity to be determined, respectively. The viscosity may also be measured by monitoring the decay in time of a vibration resonance in the pipe.

18 Claims, 3 Drawing Sheets

NON-INVASIVE FLUID DENSITY AND VISCOSITY MEASUREMENT

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to the measurement of density and viscosity of fluids and, more particularly, to the noninvasive measurement of density and viscosity of fluids using acoustic technology.

BACKGROUND OF THE INVENTION

Presently, a vibrating U-shaped-tube densitometer, where the natural mechanical frequency of vibration of the fluid-filled tube changes with varying fluid density is widely used to measure fluid density. A fluid is placed inside a vibrating U-tube and its resonance frequency is monitored. This frequency is related to the fluid density. Electromechanical elements and a feed-back loop amplifier maintain the vibrations and provide a frequency output determined by the fluid density. Such measurements require that fluid from a flowing pipe is diverted into the U-tube.

Using a quasi-steady and homogeneous fluid model, the mass of the fluid effectively adds to the mass of the U-tube/fluid system since the fluid typically has little effect on the stiffness of the system. Introducing fluid into the tube then changes the natural frequency of the oscillation of the system. The mass of the fluid in the tube is proportional to fluid density, $\rho_{fluid}$, and the natural frequency, $f_{nat}$, of the system decreases with increasing fluid density in accordance with:

$$f_{nat} = \frac{1}{2\pi}\sqrt{\frac{K_{struct}}{m_{struct}+\beta\rho_{fluid}}},$$

where, $\beta$ is a calibration constant related to the geometry and vibratory characteristic of the vibrating tube, $m_{struct}$ is the mass of the tube structure, and $K_{struct}$ is a stiffness constant related to the elastic properties of the tube material. The natural frequency of the fluid loaded tubes can be further simplified as:

$$f_{nat} = \frac{f_s}{\sqrt{1+\frac{m_{fluid}}{m_{struct}}}},$$

where $m_{fluid}$ is the mass of the fluid inside the tube.

As stated hereinabove, the resonance frequency of a pipe or a cylinder (or any shape container) changes with fluid loading. The resonance frequencies for an empty pipe and a fluid-filled pipe can be expressed as:

$$f_{empty} = \frac{1}{2\pi}\sqrt{\frac{K_{pipe}}{m_{pipe}}},$$

while $$f_{full} = \frac{1}{2\pi}\sqrt{\frac{K_{pipe}}{m_{pipe}+m_{fluid}}},$$

which can be rearranged such that the effect of fluid density inside a pipe can be expressed in terms of the natural frequency of the pipe as follows:

$$f_{full} = \frac{f_{empty}}{\sqrt{1+\frac{m_{fluid}}{m_{pipe}}}} = \frac{f_{empty}}{\sqrt{1+K_{pipe}\rho_{fluid}}}, \text{where}$$

$$K_{pipe} = \frac{V_{pipe}}{m_{pipe}}, \text{and}$$

$m_{fluid}$ is the fluid mass, $m_{pipe}$ is the mass of the pipe or cylinder, $\rho_{fluid}$ is the density of the fluid and $V_{pipe}$ is the internal volume of the pipe, $f_{full}$ is the frequency of a pipe filled with fluid, and $K_{pipe}$ is a constant related to the elastic properties of the pipe material. The subscripts refer to the fluid and the pipe. Effectively, the above procedure determines the weight of a pipe with and without a fluid inside by monitoring its natural vibration frequency, and the density may be obtained from the mass.

The commonly practiced procedure requires installing a branch in the pipe bearing the fluid to be investigated, and attaching a vibrating U-tube or a Coriolis type meter external to the pipe. This necessitates the undesirable drilling of holes in the pipe, attaching flanges and other modifications of the pipe, all invasive procedures.

In U.S. Pat. No. 6,053,041 for "Noninvasive Method For Determining The Liquid Level And Density Inside Of A Container" which issued to Dipen N. Sinha on Apr. 25, 2000 describes a noninvasive method for determining fluid density by generating a flexural acoustic wave the wall of a container using ultrasonic tone bursts, and measuring the phase difference of the detected flexural wave from that of the originally generated wave a small distance from the generated wave, the magnitude of the phase difference being related to fluid density immediately opposite the measurement position on the surface of the vessel.

SUMMARY OF THE INVENTION

Accordingly, it is an object of the present invention to provide an apparatus and method for determining the density of a fluid without having to divert the fluid from the pipe or cylinder in which the fluid is contained or flowing to a separate U-tube or other device.

Another object of the invention is to provide an apparatus and method for determining the density and viscosity of a fluid without having to divert the fluid from the pipe or cylinder in which the fluid is contained or flowing to a separate U-tube, or other device.

Yet another object of the invention is to provide an apparatus and method for noninvasively determining the density and viscosity of a fluid without having to transfer the fluid from the pipe or cylinder in which the fluid is contained or flowing to a separate U-tube or other container.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for measuring the density of a fluid in a container, the container having a wall with an outer surface, hereof, including in combination: an exciting transducer disposed on the outside surface of the container; a sweep generator for exciting the exciting transducer over a selected frequency range, whereby resonant vibrations are generated in the wall of the container; a receiving transducer disposed on outside surface of the container for receiving vibrations from the wall, the receiving transducer producing an electrical signal in response to the vibrations received thereby; and means for receiving the electrical signal from the receiving transducer and for determining the frequency of the resonant vibrations in the wall from which the density of the fluid is obtained.

In another aspect of the present invention and in accordance with its objects and purposes, the apparatus for measuring the density of a fluid in a container, the container having a wall with an outer surface, hereof, including in combination: an exciting transducer disposed on the outside surface of the container; a receiving transducer disposed on the outside surface of the container for receiving vibrations from the wall, the receiving transducer producing an electrical signal in response to the vibrations received thereby; a high-gain feedback loop in electrical contact with the exciting transducer and the receiving transducer, whereby random noise on the electrical signal is amplified and a resonant vibration mode of the container is selected; and means for receiving the electrical signal from the receiving transducer and for determining the frequency of the resonant vibration in the wall from which the density of the fluid is obtained.

In yet another aspect of the present invention and in accordance with its objects and purposes, the method for measuring the density of a fluid in a container, the container having a wall with an outer surface, hereof, includes the steps of: exciting resonant vibrations in the wall of the container; receiving vibrations from the wall, and generating an electrical signal in response to the vibrations; and receiving the electrical signal and determining the frequency of the resonant vibrations in the wall from which the density of the fluid is obtained.

In still another aspect of the present invention and in accordance with its objects and purposes, the method for measuring the density of a fluid in a container, the container having a wall with an outer surface to which surface an exciting transducer and a receiving transducer are contacted, hereof including the steps of: bringing the exciting transducer and the receiving transducer into electrical contact with a high-gain feedback loop, whereby random noise on the electrical signal is amplified and a resonant vibration mode of the pipe or the container is selected; and determining the frequency of the resonant vibration in the wall from which the density of the fluid is obtained.

In another aspect of the present invention and in accordance with its objects and purposes, the apparatus for measuring the density and viscosity of a fluid in a container, the container having a wall with an outer surface, hereof, including in combination: an exciting transducer disposed on the outside surface of the container; a receiving transducer disposed on the outside surface of the container for receiving vibrations from the wall, said receiving transducer producing an electrical signal in response to the vibrations received thereby; a high-gain feedback loop in electrical contact with the exciting transducer and the receiving transducer, whereby random noise on the electrical signal is amplified and a resonant vibration mode of the container is selected; means for receiving the electrical signal from the receiving transducer and for determining the frequency of the resonant vibration in the wall from which the density of the fluid is obtained; a band-pass filter in the high-gain feedback loop for selecting the frequency range of the high-gain feedback loop; an analog switch for disconnecting the exciting transducer from the high-gain feedback loop; and means for receiving the electrical signal and monitoring the decay of the selected resonant vibration, from which the viscosity of the fluid is determined.

Benefits and advantages of the present invention include, but are not limited to, the real-time, noninvasive and continuous monitoring of a fluid flowing through a pipe, while maintaining the integrity of the system in which the fluid is flowing, and without requiring mechanical alterations to the pipe.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Briefly, the present invention includes the noninvasive measurement of the density and viscosity of static or flowing fluids in a section of pipe such that the pipe performs as the sensing apparatus. As used herein, a pipe or a container enclosing the fluid are interchangeable. Measurement of a suitable structural vibration resonance frequency of the pipe and the width of this resonance permits the density and viscosity to be determined, respectively. The viscosity may also be measured by monitoring the decay in time of the vibration amplitude of the resonance of the pipe. Pipes have multiple vibration resonance modes; typically, the lowest vibration modes that are well below the first wall thickness mode resonance are the most sensitive for determining fluid density. Therefore, frequency scans are between about 1 kHz and about 100 kHz.

Figure 1A:
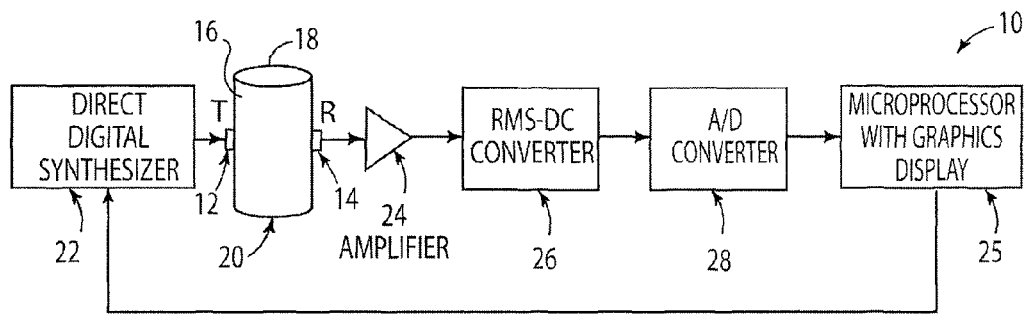
FIG. 1A is a schematic representation of one embodiment of the apparatus of the present invention for monitoring the density of a fluid in a continuous manner.

Reference will now be made in detail to the present embodiments of the invention, examples of which are illustrated in the accompanying drawings. In the Figures, similar structure will be identified using identical reference characters. Turning now to FIG. 1A, a schematic representation of one embodiment of an apparatus, 10, for monitoring the density of a fluid in a continuous manner. Piezoelectric exciting transducer, 12, and piezoelectric receiving transducer, 14, are affixed to outer surface, 16, of wall, 18, of pipe, 20, in close proximity to each other, although neither the precise location on surface 16 of pipe 20 nor the separation between the two transducers is critical. Since the entire pipe section vibrates, it does not much matter where vibration is detected. If the location chosen for the receiving transducer is a nodal point of any resonance, then the amplitude of that resonance mode is affected but the frequency may still be determined. Typically, the exciting and receiving transducers are disposed within 1 cm of each other (edge to edge). The frequency bandwidth of the transmitting transducer may be between about 1 kHz and 100 kHz which may be attached to the pipe by mechanical clamping or glue, and the like. In the case of steel pipes, the transducers may be attached magnetically.

Direct digital synthesizer integrated circuit, 22, controlled by microprocessor, 24, applies a sine-wave voltage to exciting transducer 12 effective for generating vibrations in wall 18 of pipe 20. The output from transducer 14 is amplified by amplifier, 24. A measure of the signal amplitude is obtained using root-mean-square-to-dc (RMS-DC) converter circuit, 26. For any given sine-wave amplitude, RMS-DC converter provides a DC voltage value that is related to the root-mean-square value of the sine-wave. This DC value of the signal amplitude is then digitized using analog-to-digital (A/D) converter, 28, before being stored in the memory of microprocessor 25. Microprocessor 25 may also include a graphics screen for simultaneous display. Whenever, the excitation frequency coincides with a vibration resonance mode of pipe 20, this pipe resonance mode is excited which is loaded down by the presence of the fluid and can thus be related to the density of the fluid. Often, the frequency spectrum is recorded since, as will be described in more detail hereinbelow, it contains information concerning the viscosity of the fluid as well. A typical spectrum takes less than 10 s depending on the number of points stored. Shorter times may be realized if only a small frequency range (~5 KHz) is covered and only a small number of frequency steps (~100 steps) are used which generally adequate to make the required measurements.

In another embodiment of the apparatus of the present invention, no function generator or direct digital synthesizer is required. Once the resonance characteristics of pipe 20 are determined by other measurements (the characteristics of a given system need only be measured or modeled once), a less complex measurement system can be employed. In vibration measurement apparatus, 30, illustrated in FIG. 1B hereof, if one generates high gain in feedback loop, 32, between exciting transducer 12 and receiving transducer 14, the circuit automatically locks on to the closest vibration resonance of pipe 20. Band-pass filter, 34, may be adjusted to limit the frequency range of loop 32 to the desired vibration resonances within the band pass of the filter. Generally, noise in the system picked detected by receiver transducer 14 will be amplified by high-gain amplifiers, 36a and 36b, to drive exciting transducer 12 and the circuit quickly locks on to a vibration resonance in pipe 20, the resonance frequency being continuously measured by frequency counter, 40, or any other suitable means. Frequency counter 40 may include a microprocessor such that the fluid density may be displayed in real time, if desired. Sine-waves are generated by this system because the resonance itself behaves a narrow band-pass filter, thereby only permitting sine waves to be generated and detected by receiver 14. As will be described in greater detail hereinbelow, if feedback loop 32 is opened, the amplitude of the vibration resonance in pipe 20 will decay in time. The decay time constant is exactly the reciprocal of the frequency width of the vibration resonance peak at half the maximum peak amplitude value, one being in time domain (the decay time), and the other in the frequency domain.

Pipe 20 may be calibrated by measuring the resonance frequency of any chosen vibration mode when the pipe is empty, and again when filled with a known fluid to determine the parameter $f_{empty}$, and structure constant $K_{pipe}$. Once these values are determined, unknown densities of fluids introduced into the pipe may be determined.

Figure 2:
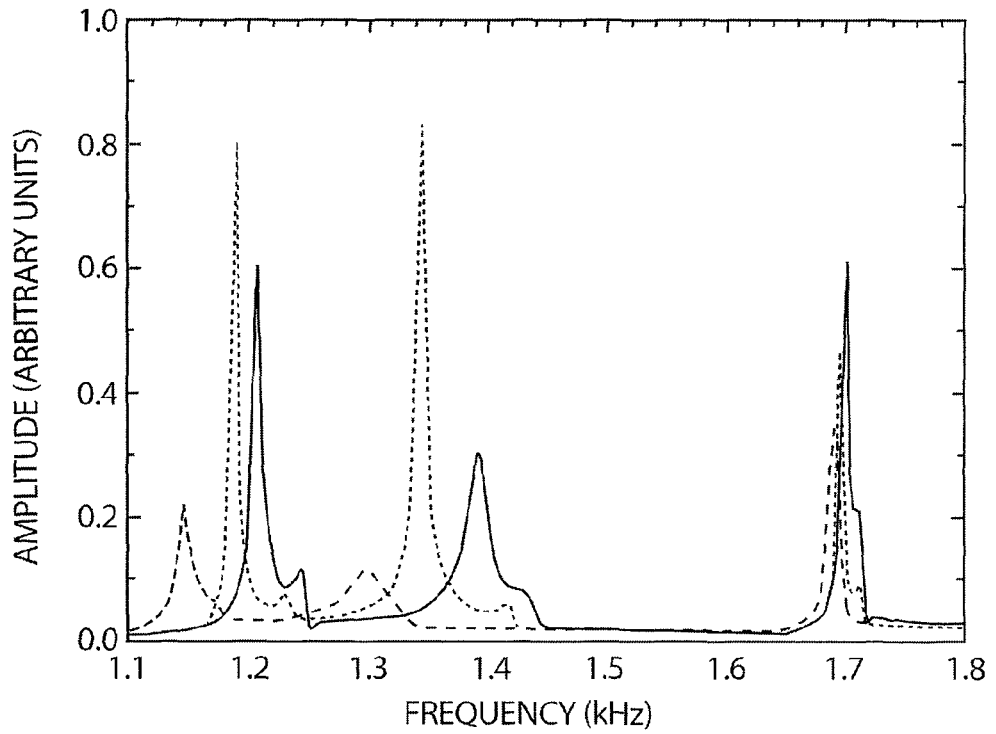
FIG. 2 is a graph of the amplitude of the received signal as a function of the excitation frequency applied to the pipe containing the fluid.

As may be observed from FIG. 2, hereof, viscous fluids dampen the resonance vibrations of a pipe; for example, corn syrup which is significantly more viscous than water yields broader peaks than does water. This dampening is the result of vibration energy leaking into the fluid inside of the pipe. Typically, the vibration resonances of a pipe have two components (one real and one imaginary) that define its characteristics. The real component contributes to the frequency shift, such as that due to mass loading of the pipe, and is therefore related to the density of the fluid. The imaginary component contributes to the attenuation or damping of the resonance peaks. This component is related to a combination of fluid viscosity, $\mu$ and density $\rho_{fluid}$ in the form of $\sqrt{\mu \rho_{fluid}}$. Since the fluid density can be determined independently from the frequency shift of the resonance, the fluid viscosity can be determined from the resonance width (full-width-at-half-maximum).

Figure 1B:
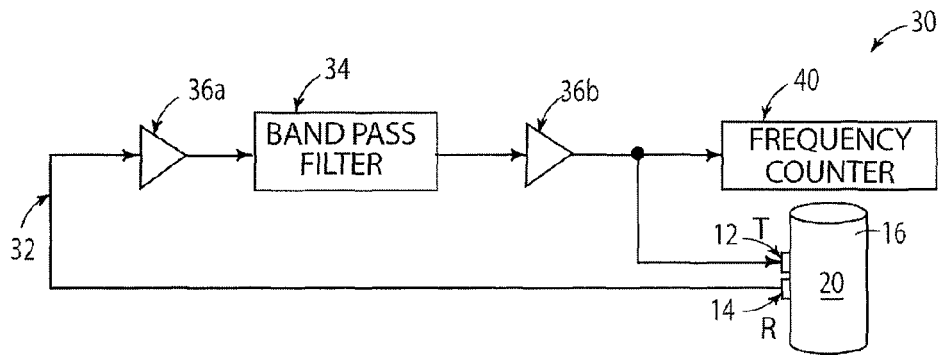
FIG. 1B is a schematic representation of another embodiment of the apparatus of the invention for monitoring the density of a fluid without the requirement of a function generator or direct digital synthesizer illustrate in FIG. 1A hereof.
Figure 1C:
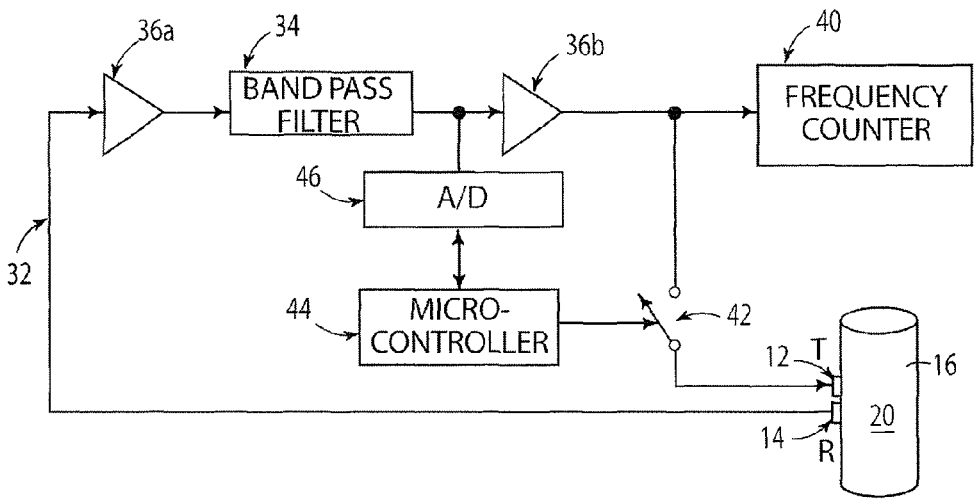
FIG. 1C is a schematic representation of an apparatus for determining both the density and viscosity of a fluid in a pipe as a modification to the apparatus illustrated in FIG. 1B hereof.

This information can also be obtained from the decay of a vibration resonance as a function of time which can be determined by breaking the feedback loop by, for example, temporarily disconnecting the signal to the exciting transducer in FIG. 1B, once the feedback loop is locked onto a resonance and then observing the decay of the receiving transducer output signal amplitude as a function of time. There are several ways of accomplishing this and one circuit for achieving this purpose is shown in FIG. 1C. Additional components to those found FIG. 1B include analog switch, 42, controlled by microcontroller, 44, and analog-to-digital (A/D) converter, 46. Microcontroller 44 monitors the signal output of band-pass filter 34 and can determine both the frequency and the amplitude of the signal. At regular intervals of time, microcontroller 44 turns off analog switch 42, thus disconnecting the power to exciting transducer whereby pipe vibration resonances will decay because they are no longer excited. A/D converter 46 processes the time evolution of this decay and microcontroller 44 calculates the decay time constant. Microcontroller 44 also determines the frequency of the resonance to determine the fluid density. From the density and the resonant amplitude decay information, the viscosity of the fluid can be determined. As stated hereinabove, the decay time constant is equal to the resonance peak width in the time domain and is related to $K_{pipe}\sqrt{\mu \rho_{fluid}}$. To determine this relationship experimentally, a known fluid, such as water, is flowed in the pipe to calibrate the system one time. Thus, it is possible to determine the fluid viscosity and density simultaneously and in a continuous, noninvasive manner.

Further, the present apparatus finds use in monitoring fluid properties where the fluid flowing through the pipe is being pumped out of the ground, as an example, such as crude oil. In the US, much of the extracted oil contains a significant amount of water, and it is important to continuously monitor both the density and the viscosity of the fluid to observe the nature of the crude oil. The oil industry presently uses several kinds of instruments to monitor the crude oil (for example, Coriolis meters), but these are invasive in that they require diversion of the fluid flow to the instrument, and expensive.

Having generally described the invention, the following EXAMPLES provide additional detail:

EXAMPLE 1

FIG. 2 is a graph of amplitude of the received vibration signal as a function of frequency for swept frequency vibration excitation applied to the pipe surface between about 1 kHz and about 1.5 kHz. Measurements were made using a 23 cm long section of a 1.8 mm thick, 7.3 cm diameter copper pipe with three fluids: corn syrup ($\rho=1.350$ g/cm$^3$), water ($\rho=0.998$ g/cm$^3$) and cooking oil (corn oil $\rho=0.922$ g/cm$^3$). The vibration modes show clear separation in resonance frequency, but the lower frequency mode showed greater resolution among the resonances and was used for the density measurement. In fact, higher modes may be used, but with different density resolutions. As stated hereinabove, the full-width-at-half-maximum of the peaks is proportional to the viscosity of the fluids.

EXAMPLE 2

Figure 3:
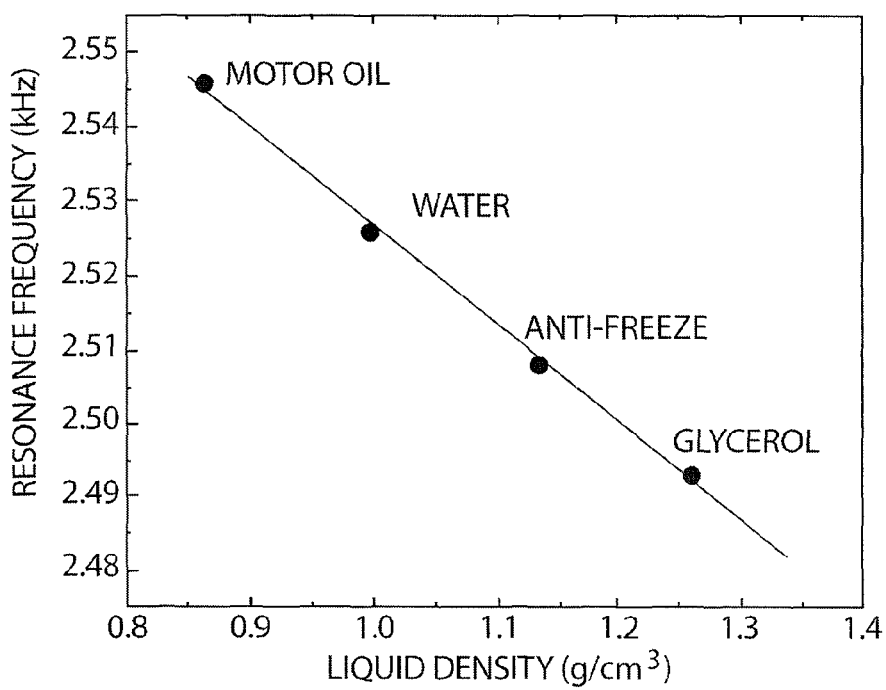
FIG. 3 is a graph of the resonance vibration frequency as a function of fluid density for four fluids.

FIG. 3 is a plot of the resonance vibration frequency as a function of fluid density for four fluids: Motor oil 10-30 ($\rho=0.863$ g/cm$^3$), water ($\rho=0.998$ g/cm$^3$), ethylene glycol (anti-freeze, $\rho=1.136$ g/cm$^3$), and glycerol ($\rho=1.350$ g/cm$^3$), for a steel pipe that has significantly greater wall thickness and is much larger than the one used in the collection of data for FIG. 2 (a 5-mm thick wall, a diameter of 15 cm, and a length of 60 cm). The measured resonance frequencies of the lowest vibration mode of the pipe are shown as dots, and the curve fit to the data with using theory is shown as the solid line. The theoretical form for the equation is the same as that set forth hereinabove for the vibrating tube densitometer, and illustrates that the behavior of the density measurements in a pipe follows the same form. The measured resonance frequency of the empty pipe is 2.7 kHz which is in good agreement with that derived from the curve fit of the data (2.673 kHz).

EXAMPLE 3

Figure 4:
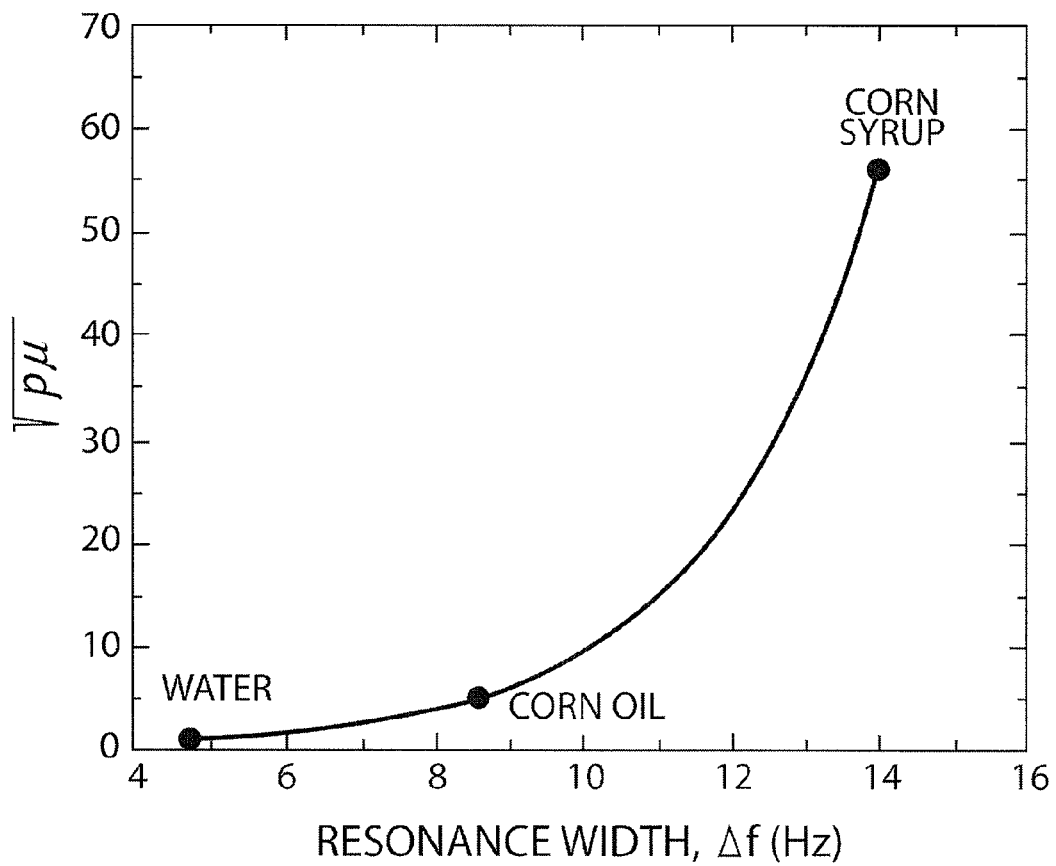
FIG. 4 is a graph of the fluid viscosity plotted as $\sqrt{\mu \rho_{fluid}}$, as a function of the widths, $\Delta f$ of the first resonances of the fluids as graphed in FIG. 2 hereof.

FIG. 4 is a graph of the fluid viscosity plotted as $\sqrt{\mu \rho_{fluid}}$, as a function of the widths, $\Delta f$ of the first resonances for the fluids shown in FIG. 2 hereof. The experimental data are shown by the black dots, and a plot the equation:

$$\sqrt{\rho_{fluid}\mu} = 0.15 + 0.112 \exp\left(\frac{\Delta f}{2.254}\right),$$

using literature values for $\sqrt{\mu \rho_{fluid}}$ fits the experimental data well. As stated hereinabove, the decay time-constants measured in the experiment and the resonance widths are related and provide the same information, one being in the frequency domain and the other in the time domain. The equation parameters are slightly different for the second set of resonance peaks shown in FIG. 2 hereof because of different sensitivity, but the form is the same.

Thus, attenuation by a fluid in a pipe clearly damps vibration resonance curves. This effect manifests itself in two different ways: (1) the width of the resonance is broadened as the density of the enclosed fluid increases; and (2) the amplitude of the resonance peaks diminish, both of which are related. Further, the amplitude of the vibration resonances decays exponentially as a function of time which is the time domain analog of a frequency domain (resonance measurement), $$\text{or } \Delta f = \frac{const}{\Delta T};$$

thus both types of measurements yield same information.

EXAMPLE 4

The present invention has been used to monitor polymerization in fluids, by monitoring the resonance spectrum of a glass test tube containing the fluid as a function of time, while the temperature of the fluid was changed. The tube was clamped between spring-loaded piezoelectric exciting and receiving transducers. A resonance spectrum was obtained by sweeping the frequency of a sine wave signal applied to the exciting transducer between 1 kHz and 100 kHz. The spectrum of the unpolymerized fluid showed sharp resonances which dramatically changed as the fluid polymerized and became viscous. The resonance peaks virtually disappeared and the spectrum became damped.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for measuring the density of a fluid in a container, said container having a wall with an outer surface, comprising in combination:
    a sensing apparatus, wherein said sensing apparatus is a section of the container;
    an exciting transducer disposed on the outside surface of said container;
    a sweep generator for exciting said exciting transducer over a selected frequency range, whereby resonant vibrations are generated in the wall of said container;
    a receiving transducer disposed on outside surface of said container for receiving vibrations from the wall, said receiving transducer producing an electrical signal in response to the vibrations received thereby; and
    means for receiving the electrical signal from said receiving transducer and for determining the frequency of the resonant vibrations and continuously tracking the resonance peak frequency in the wall from which the density of the fluid is obtained.

2. The apparatus of claim 1, further comprising means for measuring the full-width-at-half-maximum of the resonant vibrations from which the viscosity of the fluid is obtained.

3. The apparatus of claim 1, wherein the selected frequency range is between 1 kHz and 100 kHz.

4. Apparatus for measuring the density of a fluid in a container, said container having a wall with an outer surface, comprising in combination:

a sensing apparatus, wherein said sensing apparatus is a section of the container;

an exciting transducer disposed on the outside surface of said container;

a receiving transducer disposed on the outside surface of said container for receiving vibrations from the wall, said receiving transducer producing an electrical signal in response to the vibrations received thereby;

a high-gain feedback loop in electrical contact with said exciting transducer and said receiving transducer, whereby random noise on the electrical signal is amplified and a resonant vibration mode of said container is automatically selected; and means for receiving the electrical signal from said receiving transducer and for determining the frequency of the resonant vibration and continuously tracking the resonance peak frequency in the wall from which the density of the fluid is obtained.

5. The apparatus of claim 4, further comprising a band-pass filter in said high-gain feedback loop for selecting the frequency range of said high-gain feedback loop.

6. The apparatus of claim 5, further comprising an analog switch for disconnecting said exciting transducer from said high-gain feedback loop; and means for receiving the electrical signal and monitoring the decay of the selected resonant vibration, from which the viscosity of the fluid is determined.

7. The apparatus of claim 5, wherein the selected frequency range is between 1 kHz and 100 kHz.

8. A method for measuring the density of a fluid in a container, the container having a wall with an outer surface, comprising the steps of:

making the measurement while the fluid is flowing through the container itself;

exciting resonant vibrations in the wall of the container;

receiving vibrations from the wall, and generating an electrical signal in response to the vibrations;

receiving the electrical signal and determining the frequency of the resonant vibrations in the wall from which the density of the fluid is obtained; and continuously tracking the resonance peak frequency.

9. The method of claim 8, the step of measuring the full-width-at-half-maximum of the resonant vibrations from which the viscosity of the fluid is obtained.

10. The apparatus of claim 8 wherein the selected frequency range is between 1 kHz and 100 kHz.

11. A method for measuring the density of a fluid in a container, the container having a wall with an outer surface to which surface an exciting transducer and a receiving transducer are contacted, comprising the steps of:

making the measurement while the fluid is flowing through the container itself;

bringing the exciting transducer and the receiving transducer into electrical contact with a high-gain feedback loop, whereby random noise on the electrical signal is amplified and a resonant vibration mode of the pipe or the container is selected;

determining the frequency of the resonant vibration in the wall from which the density of the fluid is obtained; and continuously tracking the resonance peak frequency.

12. The method of claim 11, further comprising the step of a selecting the frequency range of the high-gain feedback loop.

13. The method of claim 11, further comprising the steps disconnecting the exciting transducer from the high-gain feedback loop; and monitoring the decay of the selected resonant vibration from which the viscosity of the fluid is determined.

14. The method of claim 12, wherein the selected frequency range is between 1 kHz and 100 kHz.

15. The method of claim 12, wherein the frequency is selected using a band-pass filter in the high-gain feedback loop.

16. The method of claim 13, wherein an analog switch is employed for disconnecting the exciting transducer from the high-gain feedback loop.

17. Apparatus for measuring the density and viscosity of a fluid in a container, said container having a wall with an outer surface, comprising in combination:

a sensing apparatus, wherein said sensing apparatus is a section of the container;

an exciting transducer disposed on the outside surface of said container;

a receiving transducer disposed on the outside surface of said container for receiving vibrations from the wall, said receiving transducer producing an electrical signal in response to the vibrations received thereby;

a high-gain feedback loop in electrical contact with said exciting transducer and said receiving transducer, whereby random noise on the electrical signal is amplified and a resonant vibration mode of said container is automatically selected;

means for receiving the electrical signal from said receiving transducer and for determining the frequency of the resonant vibration and continuously tracking the resonance peak frequency in the wall from which the density of the fluid is obtained;

a band-pass filter in said high-gain feedback loop for selecting the frequency range of said high-gain feedback loop;

an analog switch for disconnecting said exciting transducer from said high-gain feedback loop; and means for receiving the electrical signal and monitoring the decay of the selected resonant vibration, from which the viscosity of the fluid is determined.

18. The apparatus of claim 17, wherein the selected frequency range is between 1 kHz and 100 kHz.

* * * * *